United States Patent [19]
Kielpikowski

[11] Patent Number: 6,056,733
[45] Date of Patent: May 2, 2000

[54] ELASTICIZED CONTAINMENT FLAPS

[75] Inventor: David Peter Kielpikowski, Appleton, Wis.

[73] Assignee: Kimberly-Clark Worldwide, Inc., Neenah, Wis.

[21] Appl. No.: 08/421,131

[22] Filed: Apr. 13, 1995

Related U.S. Application Data

[63] Continuation of application No. 08/160,521, Dec. 1, 1993, abandoned.

[51] Int. Cl.⁷ ..................................................... A61F 13/15
[52] U.S. Cl. ..................................... 604/385.2; 604/385.1
[58] Field of Search ............................. 604/385.1, 385.2; 2/75, 76, 78.3, 401; 66/192, 196, 202; 428/102

[56] References Cited

U.S. PATENT DOCUMENTS

| | | | |
|---|---|---|---|
| 2,544,069 | 3/1951 | Cutler | 128/287 |
| 2,681,019 | 6/1954 | Liebowitz | 112/2 |
| 3,039,466 | 6/1962 | Wilson | 128/287 |
| 3,663,962 | 5/1972 | Burger | 2/224 |
| 3,694,815 | 10/1972 | Burger | 2/224 |
| 4,297,157 | 10/1981 | Van Vliet | 156/164 |
| 4,674,135 | 6/1987 | Greene | 2/406 |
| 4,695,278 | 9/1987 | Lawson | 604/385.2 |
| 4,704,116 | 11/1987 | Enloe | 604/385 A |
| 4,704,321 | 11/1987 | Zafiroglu | 428/230 |
| 4,729,131 | 3/1988 | Thygeser | 2/400 |
| 4,773,238 | 9/1988 | Zafiroglu | 66/192 |
| 4,879,169 | 11/1989 | Zafiroglu | 428/230 |
| 4,900,384 | 2/1990 | Sanders et al. | 156/204 |
| 4,998,421 | 3/1991 | Zafiroglu | 66/192 |
| 5,087,255 | 2/1992 | Sims | 604/385.1 |

OTHER PUBLICATIONS

Havley's Condensed Chemical Dictionary, 11th ed, Definitions of "Acetate Fiber", "Cellutose Acetate", "Rayon", pp. 6, 237, 997.

*Primary Examiner*—John G. Weiss
*Assistant Examiner*—K. M. Reichle
*Attorney, Agent, or Firm*—Jeffrey B. Curtin

[57] ABSTRACT

Disclosed is a containment flap for use on an absorbent article. The containment flap has a proximal edge which is joined to the absorbent article and an opposite distal edge. The containment flap includes a barrier layer which is stitched with at least one elastomeric thread adjacent the distal edge of the containment flap. Also disclosed is an absorbent article including such a containment flap and a method of making such an absorbent article.

10 Claims, 3 Drawing Sheets

ELASTICIZED CONTAINMENT FLAPS

This is a continuation of application Ser. No. 08/160521 filed on Dec. 1, 1993, now abandoned.

BACKGROUND OF THE INVENTION

1. Technical Field

The present invention relates to elasticized containment flaps and their construction. Specifically, the present invention relates to containment flaps used to improve the containment of body exudates in absorbent articles.

2. Description of the Related Art

Absorbent articles such as infant diapers, training pants, sanitary napkins, adult incontinence products and the like are well known. Such articles have achieved a wide acceptance due to their ability to absorb body exudates without leaking. In order to achieve a high degree of leakage protection, it has become increasingly common to rely on systems wherein numerous components cooperate. For example, in the case of infant diapers, urine is generally absorbed by an absorbent core comprising a matrix of wood pulp fluff and superabsorbent material. Such an absorbent core is known to be particularly well suited for absorbing and holding urine in a diaper structure. Unfortunately, it is not always possible for the absorbent core to absorb and hold urine at the rate at which it is delivered. Thus, it has become increasingly common to rely on various mechanical containment means to hold urine within the diaper until it can be absorbed and held by the absorbent core.

For example, it is well known to those skilled in the art to provide elasticized leg cuffs along the leg openings of a diaper. The leg cuffs are said to assist in the containment of body exudates. Similarly, it is well known to those skilled in the art to use waist elastics in a diaper to obtain a tighter seal about the waist of a wearer. The waist elastics also contribute to the mechanical containment of body exudates.

In an attempt to improve the mechanical containment of body exudates, it is also known to employ a pair of containment flaps along the longitudinal sides of absorbent articles such as infant diapers, training pants, sanitary napkins, adult incontinence products and the like. Such containment flaps are shown in U.S. Pat. No. 4,704,116 issued Nov. 3, 1987, to Enloe. The containment flaps are generally thought to be particularly well suited for the containment of fecal matter and the prevention of lateral flow of liquid waste until the liquid waste can be absorbed by the absorbent article. Elasticized leg cuffs are often used in conjunction with the containment flaps to help contain body exudates.

Containment flaps generally include a proximal edge which is attached to the absorbent article and an opposite distal edge which is generally not attached to the absorbent article along at least a portion of its length. Each of the containment flaps may also include elastic members which are generally located adjacent the distal edge to provide a sealing relationship by conforming the distal edge to the shape of the wearer during use. The elastic members also assist in maintaining the containment flaps in an upright position during use. Typically, the elastic members are attached to the containment flaps by folding the material of the containment flap in a longitudinal direction over the elastic members and back upon itself. The folded over portion of the containment flap is secured to another portion of the containment flap thereby forming a hem that contains the elastic members. For example, the folded over portion of the containment flaps may be secured by adhesive or ultrasonic bonding.

However, the methods of attaching the elastic members to the containment flaps as described above tend to undesirably affect the stiffness of the containment flaps. The double layer of material which provides the hem that contains the elastic members and the bonding of the hem to the containment flap undesirably reduces the flexibility and increases the stiffness of the containment flaps. Adhesive and ultrasonic bonding also reduce the flexibility and increase the stiffness of the containment flaps. Containment flaps that are too stiff do not conform to the shape of the wearer as snugly as desired and may irritate the skin of the wearer. The lack of a sealing relationship between the distal edge of the containment flap and the body of the wearer tends to decrease the effectiveness of the containment flaps in containing body exudates. Moreover, a certain amount of the elastic nature of the elastic member may be destroyed if the elastic member is bonded to the containment flap. Specifically, at the points where the elastic member is attached to the containment flap, the elastic member is no longer capable of being stretched. That is, it is no longer "elastic".

Accordingly, it is desired to provide containment flaps that are generally flexible and provide an improved fit and containment of body exudates in absorbent articles that employ such containment flaps.

SUMMARY OF THE INVENTION

In response to the discussed difficulties and problems encountered in the prior art a new containment flap and absorbent article including a pair of the containment flaps has been discovered.

In one aspect, the present invention concerns a containment flap for use on an absorbent article. The containment flap has a length, a proximal edge which is adapted to be joined to the absorbent article and a distal edge which is opposite the proximal edge. The containment flap includes a barrier layer which is stitched with at least one elastomeric thread adjacent the distal edge of the containment flap. In a specific embodiment of the containment flap, the barrier layer is stitched with an elastomeric thread that is elongated.

In another aspect, the present invention concerns an absorbent article having a front portion, a rear portion and a crotch portion connecting the front and rear portions. The crotch portion has opposite longitudinal side portions. The absorbent article includes a liquid-permeable bodyside liner, an outer cover, and an absorbent core which is located between the bodyside liner and the outer cover. A pair of elasticized longitudinally extending leg cuffs are located at the opposite longitudinal side portions of the crotch portion. A pair of containment flaps extend longitudinally from the front portion of the absorbent article to the rear portion. The containment flaps have a proximal edge, a distal edge which is opposite the proximal edge, a width and a length. The proximal edge is joined to the bodyside liner in the crotch portion and the front and rear portions. Each of the containment flaps includes a barrier layer which is stitched with at least one elastomeric thread adjacent the distal edge of the containment flap. In a specific embodiment of this absorbent article, the barrier layer of the containment flap is stitched with an elastomeric thread that is elongated.

In yet another aspect, the present invention concerns a method of making an absorbent article. A liquid-permeable bodyside liner which has a front portion, a rear portion and a crotch portion is provided. The crotch portion has opposite longitudinal side portions and connects the front and rear portions. An outer cover is placed in a facing relationship with the bodyside liner. An absorbent core is placed between the bodyside liner and the outer cover and the bodyside liner and outer cover are joined together. A pair of elasticized longitudinally extending leg cuffs are joined to the bodyside liner at the opposite longitudinal side portions of the crotch portion. Finally, a pair of barrier layers are provided. Each barrier layer is stitched with at least one elastomeric thread to provide a pair of containment flaps. The containment flaps are then joined to the bodyside liner in the crotch portion and the front and rear portions. In a specific embodiment of this method, the barrier layer is stitched with an elastomeric thread that is elongated.

DETAILED DESCRIPTION OF THE PREFERRED EMBODIMENT

The present invention relates to containment flaps that are adapted for use on absorbent articles and a method for making the absorbent articles. Such containment flaps are generally employed along the longitudinal sides of absorbent articles such as infant diapers, training pants, sanitary napkins, adult incontinent products and the like to improve the containment of body exudates.

Figure 1:
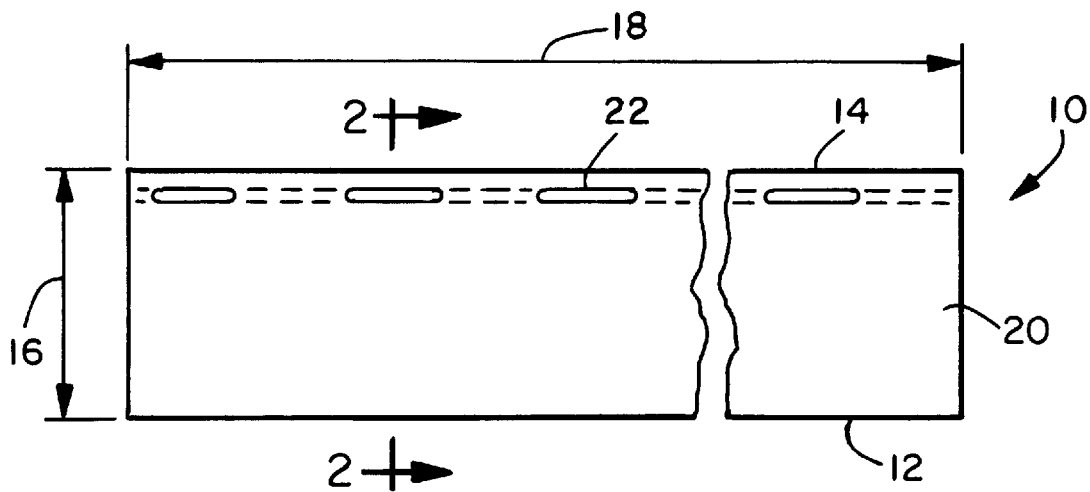
FIG. 1 is a front elevational view of a containment flap according to the present invention.
Figure 2:
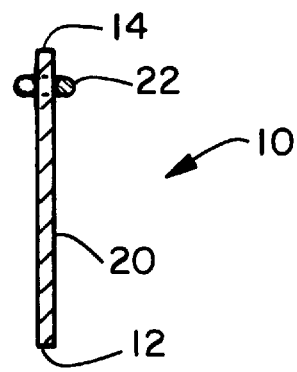
FIG. 2 is a cross-sectional view of the containment flap illustrated in FIG. 1 taken along line 2—2.
Figure 3:
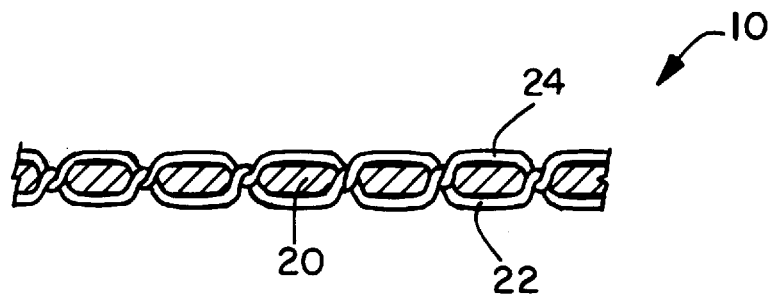
FIG. 3 is a top plan view of a containment flap according to the present invention which illustrates an alternative stitching arrangement.
Figure 4:
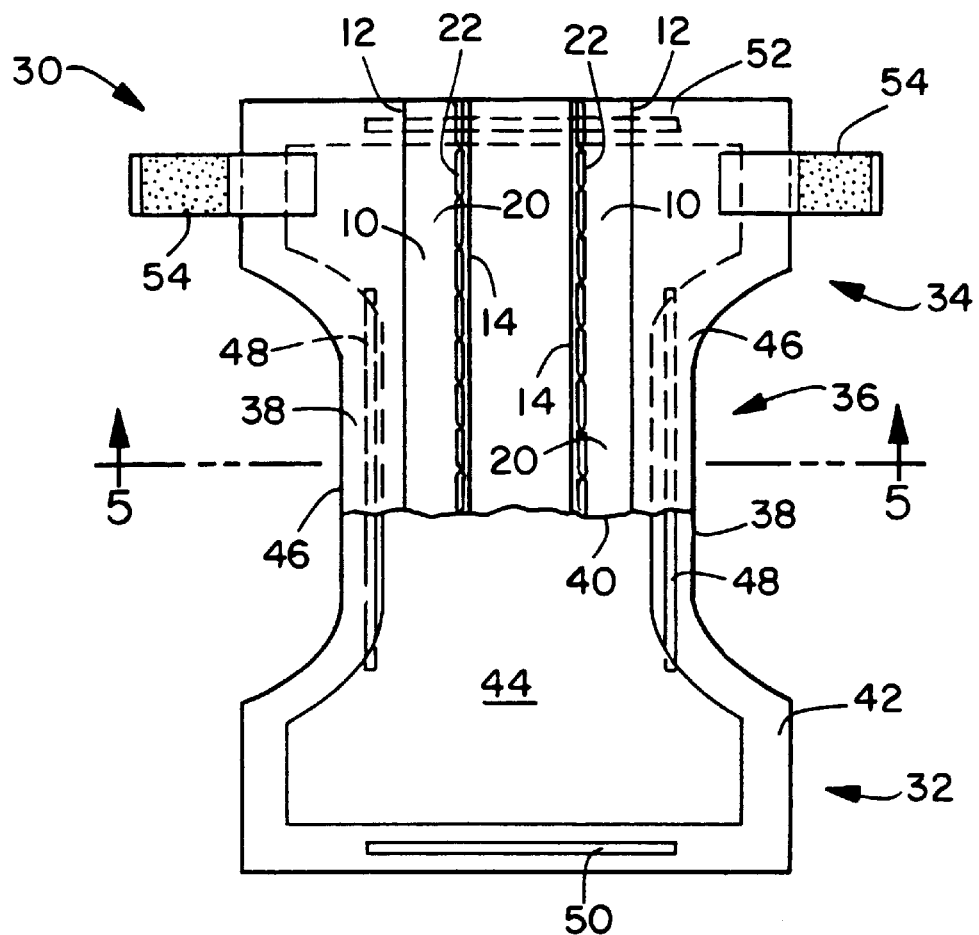
FIG. 4 is a top plan view of an absorbent article according to the present invention having portions cut away to reveal underlying structure.
Figure 5:
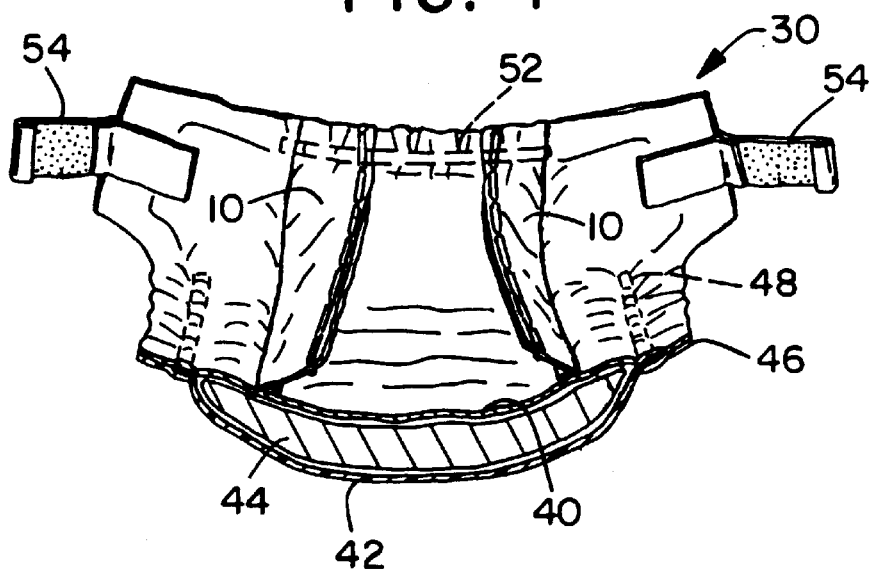
FIG. 5 is a perspective cross-sectional view of the absorbent article illustrated in FIG. 4 taken along line 5—5.

The present invention can best be understood by reference to the drawings in which like numerals represent like elements. FIG. 1 illustrates a front elevational view of a containment flap suitable for use on an absorbent article. FIG. 2 illustrates a cross-sectional view of the containment flap illustrated in FIG. 1 taken along line 2—2. FIG. 3 illustrates a partial cutaway of a top plan view of another embodiment of a containment flap of the present invention. As illustrated in FIGS. 1–3, a containment flap 10 has a proximal edge 12 which is adapted to be joined to an absorbent article, a distal edge 14 which is opposite the proximal edge 12, a width 16 and a length 18 which is generally perpendicular to the width 16. The containment flap 10 comprises a barrier layer 20 which is stitched by at least one elastomeric thread 22 adjacent the distal edge 14 of the containment flap 10.

The containment flap, as representatively illustrated in FIGS. 1–3, can be adapted for use in an absorbent article. Typically, a pair of containment flaps 10 will be attached to the absorbent article at or adjacent the proximal edge 12 of each containment flap 10. At least a portion of the distal edge 14 of each containment flap 10 is not attached to the absorbent article such that the containment flap 10 provides a barrier to the lateral flow of waste material.

A wide range of materials are suitable for use as the barrier layer 20 of the containment flap 10 as representatively illustrated in FIGS. 1–3. For example, the barrier layer 20 can include a nonwoven material such as a spunbond, meltblown, spun laced or carded polymeric material, a film material such as a polyolefin or polyurethane film, a foam material or combinations thereof. In a specific embodiment, the barrier layer 20 is formed from a nonwoven material such as a spunbond or meltblown polyethylene or polypropylene material. Many nonwoven materials are formed from hydrophobic materials. Such hydrophobic materials result in nonwovens which are somewhat resistant to the flow of liquids. If it is desired to provide a containment flap 10 having a barrier layer 20 that is generally liquid pervious, such nonwoven materials may be treated with a surfactant to render them generally hydrophilic.

Alternatively, if it is desired to provide a containment flap 10 having a barrier layer 20 that is generally liquid impervious, the barrier layer 20 can include a liquid-impervious film such as a polyolefin film.

In one specific embodiment, the barrier layer comprises a spunbond polypropylene material having a basis weight of about 25 grams per square meter and being formed from fibers having a denier of about 2.5 to 3.8. The barrier material can be treated with a surfactant such as Triton X-102, which is commercially available from Rohm and Haas Co., at an add-on rate of about 0.3 percent.

As described above the containment flap 10 includes a barrier layer 20 which is stitched with at least one elastomeric thread 22 adjacent the distal edge 14 of the containment flap 10. The barrier layer 20, as representatively illustrated in FIGS. 1–3, can be stitched with the elastomeric thread 22 by any of the processes well known to those skilled in the art, such as by hand. Alternatively, the barrier layer 20 can be stitched with the elastomeric thread 22 by a conventional industrial sewing machine such as those commercially available from Juki America, Inc., Brother International Corp. or The Singer Co. Typically, industrial sewing machines use the combination of two threads that enter opposing sides of the material being stitched and actively engage each other thereby securing both threads to the material. For example, as representatively illustrated in FIG. 3, the barrier layer 20 is stitched with the combination of an elastomeric thread 22 and a second thread 24 which enter the barrier layer 20 from opposing sides and actively engage each other to secure both threads to the barrier layer 20. When using an industrial sewing machine as described above, the second thread 24 may also be an elastomeric thread or it can be an inelastic thread.

As representatively illustrated in FIGS. 1–3, the barrier layer 20 is stitched with a single elastomeric thread 22 adjacent the distal edge 14 of the containment flap 10. Alternatively, the barrier layer 20 may be stitched with from about 2 to about 10 elastomeric threads. Multiple elastomeric threads may be configured in a laterally spaced, generally parallel arrangement. Suitably, the elastomeric thread 22 or threads are configured parallel to the distal edge 14 of the containment flap 10 and are located within about one inch (25 mm) of the distal edge 14.

The elastomeric thread 22 suitably comprises any elastomeric material capable of being elongated at least about 50 percent, desirably about 350 percent, and capable of recovering to within at least about 250 percent, desirably about 150 percent of its original length after being elongated about 300 percent. In one specific embodiment, the elastomeric thread can, for example, be composed of a spandex elastomeric thread such as, for example, a 470 decitex LYCRA thread commercially available from E.I. Dupont de Nemours and Co. Alternatively, the elastomeric thread 22 can be composed of a thermoplastic elastomer or a natural or synthetic rubber commercially available from J.P.S. Elastomerics Corp. The elastomeric thread 22 can also be composed of a heat activatable elastic material such as PEBAX, commercially available from Atochem, Inc., which can be activated with heat treatment after the barrier layer 20 is stitched with the thread 22.

In a specific embodiment of the present invention, the barrier layer 20, as representatively illustrated in FIGS. 1–3, can be stitched with an elastomeric thread 22 substantially along the entire length 18 of the containment flap 10. Alternatively, the barrier layer 20 can be stitched with the elastomeric thread 22 along a portion of the length 18 of the containment flap 10. For example, the barrier layer 20 may be stitched along at least about 60 percent of the length 18 of the containment flap 10. The ends of the elastomeric thread can be attached to the barrier layer by any method known to those skilled in the art such as thermal bonding, adhesive bonding, ultrasonic bonding, knotting or the like. Alternatively, the ends of the elastomeric thread may be contained when the barrier layer is attached to an absorbent article.

The spacing and configuration of the stitches of the elastomeric thread 22 can be varied to obtain the desired elasticity in the containment flap 10. For example, the stitches may be inserted at a spacing of from about 25 stitches per inch (about 1 stitches per mm) to about 4 stitches per inch (about 1 stitch per 6 mm) and desirably from about 15 stitches per inch (about 1 stitch per 2 mm) to about 8 stitches per inch (about 1 stitch per 3 mm). Alternatively, the spacing of the stitches may vary along the length 18 of the containment flap 10. Moreover, the stitches can be arranged in a wide variety of geometric configurations known to those skilled in the art. For example, the stitches can be arranged in a linear, curvilinear or zig-zag configuration. If the barrier layer 20 is stitched with more than one elastomeric thread 22, the spacing and configuration of the stitches of each elastomeric thread can be the same or different.

The distal edge 14 of the containment flap 10 is suitably contractible or gatherable. To provide such a containment flap, the elastomeric thread 22 is suitably stitched adjacent the distal edge 14 of the containment flap 10 while the elastomeric thread 22 is elongated such that the elastomeric thread 22 is elastically contractible. Thus, in an unrestrained condition, the elastomeric thread 22 tends to contract and gather the distal edge 14 of the containment flap 10. In a specific embodiment of the present invention, the elastomeric thread 22 is elongated from about 50 to about 300 percent and desirably from about 100 to about 250 percent as the barrier layer 20 is stitched with the elastomeric thread 22. Alternatively, the barrier layer 20 may be pleated and then stitched with an elastomeric thread 20 that is not elongated or only slightly elongated. Such a containment flap 10 can then be stretched as it is attached to an absorbent article.

Suitably, the containment flap 10, as representatively illustrated in FIGS. 1–3, comprises a barrier layer 20 which is a single layer of material and is stitched by a single elastomeric thread 22 adjacent the distal edge 14 of the containment flap 10. Such a containment flap 10 is generally less stiff and more flexible than containment flaps comprising two or more layers of material or containment flaps which are formed using adhesives or ultrasonic bonding.

The width 16 and length 18 of the containment flap 10 can vary depending on the type and size of the absorbent article to which it will be attached. In a specific embodiment, the containment flap 10 has an overall width 16 of at least about 0.5 inches (about 12 mm) and desirably from about 1 inch (about 25 mm) to about 2 inches (about 50 mm) and an overall length of at least about 8 inches (about 203 mm) and desirably from about 14 inches (about 356 mm) to about 20 inches (about 508 mm).

FIGS. 4–8 representatively illustrate an absorbent article 30 according to the present invention. The preferred embodiments of the present invention will be described in terms of an absorbent article adapted to be worn by infants about the lower torso. It is understood that the present invention is equally applicable to other absorbent articles such as adult incontinent products, training pants, feminine care products and the like. As representatively illustrated in FIGS. 4–8, the absorbent article 30 defines a front portion 32, a rear portion 34, and a crotch portion 36 connecting the front portion 32 and the rear portion 34. The absorbent article 30 includes a bodyside liner 40, an outer cover 42 and an absorbent core 44 located between the bodyside liner 40 and the outer cover 42. As used herein, reference to a front portion refers to that part of the absorbent article which is generally located on the front of a wearer when in use. Reference to the rear portion refers to the portion of the article generally located at the rear of the wearer when in use, and reference to the crotch portion refers to that portion which is generally located between the legs of the wearer when in use.

The crotch portion 36 has opposite longitudinal side portions 38 which include a pair of elasticized, longitudinally-extending leg cuffs 46. The leg cuffs 46 are generally adapted to fit about the legs of a wearer in use and serve as a mechanical barrier to the lateral flow of body exudates. The leg cuffs 46 are elasticized by a pair of leg elastics 48. The absorbent article 30 further includes a front waist elastic 50 and a rear waist elastic 52. The rear portion 34 of the absorbent article 30 further includes a fastening means such as a pair of tape fasteners 54. The tape fasteners 54 are intended to hold the absorbent article 30 about the waist of the wearer when in use.

Further, the absorbent article 30, as representatively illustrated in FIGS. 4–8, includes a pair of containment flaps 10 such as those representatively illustrated in FIGS. 1–3. Each of the containment flaps 10 extend longitudinally from the front portion 32 to the rear portion 34 of the absorbent article 30. The containment flaps 10 have a proximal edge 12 and a distal edge 14. The proximal edge 12 of each containment flap 10 is joined to the bodyside liner 40 at least in a portion of the crotch portion 36 of the absorbent article 30. Desirably, the proximal edge 12 is joined to the bodyside liner 40 along the entire length of the containment flap 10. The distal edge 14 of each containment flap 10 is joined to the bodyside liner 40 of the absorbent article 30 in at least a portion of the front portion 32 and the rear portion 34 of the absorbent article 30. The distal edge 14 is not joined to the bodyside liner 40 in at least a portion of the crotch portion 36.

Figure 6:
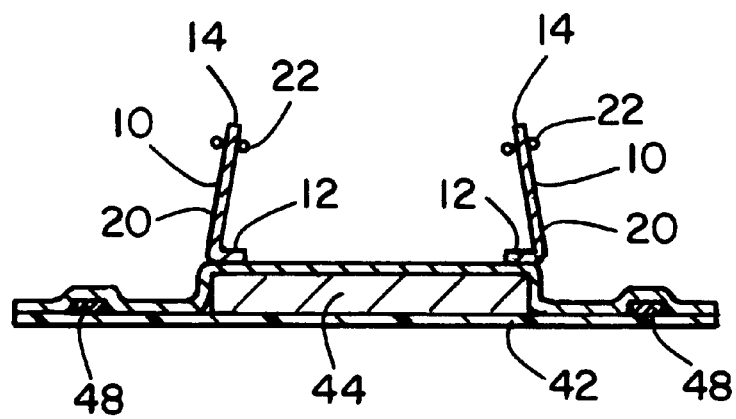
FIG. 6 is a cross-sectional view through the crotch portion of the absorbent article illustrated in FIG. 4.
Figure 7:
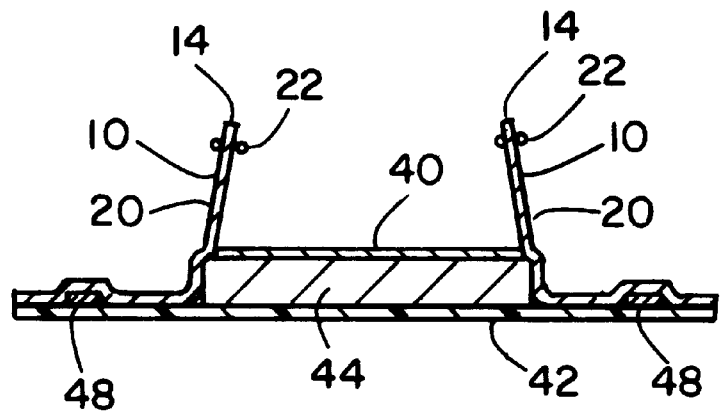
FIG. 7 is a cross-sectional view through the crotch portion of an absorbent article of the present invention which illustrates an alternative attachment of the containment flaps.
Figure 8:
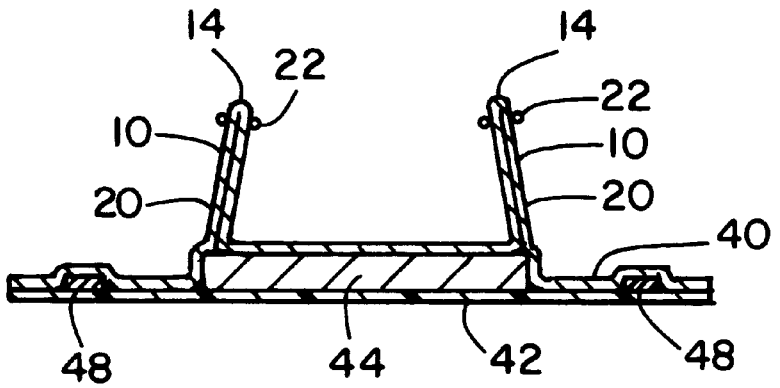
FIG. 8 is a cross-sectional view through the crotch portion of an absorbent article of the present invention which illustrates another alternative attachment of the containment flaps.

As representatively illustrated in FIG. 6, the containment flaps 10 may be formed separate from the bodyside liner 40 and joined thereto. As described above, the containment flap may be formed to be either liquid pervious or liquid impervious. Methods of joining the containment flaps 10 to the bodyside liner 40 are known to those skilled in the art.

Suitable methods include heat sealing, sonic bonding, adhesive bonding, and the like. It is generally preferred that the containment flap 10 be attached to the bodyside liner 40 close to a lateral edge of the absorbent core 44 in the crotch portion 36 of the absorbent article 30. Alternatively, as representatively illustrated in FIG. 7, the containment flaps 10 may extend beyond the longitudinal sides of the absorbent core 44 and be attached to the outer cover 42. In such a configuration, the bodyside liner 40 extends between and is attached to the containment flaps 10. In another alternative embodiment as representatively illustrated in FIG. 8, the containment flaps 10 may be integrally formed with the bodyside liner 40. Thus, the bodyside liner 40 may extend from the longitudinal sides of the absorbent article 30 to the absorbent core 44 where the bodyside liner 40 can extend upwardly and be folded over upon itself to form the containment flaps 10.

The distal edges 14 of the containment flaps 10 are desirably elasticized by an elastomeric thread 22 in at least a portion of the. crotch portion 36 and, more desirably, along the entire length of the containment flap 10. As representatively illustrated in FIGS. 1–3, each of the containment flaps 10 comprise a barrier layer 20 which is stitched with the elastomeric thread 22 adjacent the distal edge 14 of the containment flap 10. As a result, the distal edge 14 of each containment flap 10 tends to contract or gather and position itself in a spaced relation away from the bodyside liner 40 toward a generally upright and approximately perpendicular configuration in especially the crotch portion 36 of the absorbent article 30. As can be seen from reference to FIGS. 6–8, the containment flaps 10 are maintained in a relatively upright position in the crotch portion 36 of the absorbent article 30.

The bodyside liner 40 of the absorbent article 30, as representatively illustrated in FIGS. 4–8, suitably presents a body-facing surface which is compliant, soft-feeling and nonirritating to the wearer's skin. Further, the bodyside liner 40 may be less hydrophilic than the absorbent core 44, to present a relatively dry surface to the wearer, and may be sufficiently porous to be liquid permeable, permitting liquid to readily penetrate through its thickness. A suitable bodyside liner 40 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 40 is suitably employed to help isolate the wearer's skin from liquids held in the absorbent core 44.

Various woven and nonwoven fabrics can be used for the bodyside liner 40. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 40 comprises a nonwoven, spunbond, polypropylene fabric composed of about 2.8–3.2 denier fibers formed into a web having a basis weight of about 22 grams per square meter and a density of about 0.06 gram per cubic centimeter. The fabric is surface treated-with about 0.28 weight percent of a surfactant commercially available from Rohm and Haas Co. under the trade designation Triton X-102.

The outer cover 42 of the absorbent article 30, as representatively illustrated in FIGS. 4–8, may suitably be composed of a material which is either liquid permeable or liquid impermeable. It is generally preferred that the outer cover 42 be formed from a material which is substantially impermeable to liquids. For example, a typical outer cover can be manufactured from a thin plastic film or other flexible liquid-impermeable material. For example, the outer cover 42 may be formed from a polyethylene film having a thickness of from about 0.012 millimeter (0.5 mil) to about 0.051 millimeter (2.0 mils). If it is desired to present the outer cover 42 with a more clothlike feeling, the outer cover 42 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). Methods of forming such clothlike outer covers are known to those skilled in the art.

Further, the outer cover 42 may be formed of a woven or nonwoven fibrous web layer which has been totally or partially constructed or treated to impart a desired level of liquid impermeability to selected regions that are adjacent or proximate the absorbent core 44. Still further, the outer cover 42 may optionally be composed of a micro-porous "breathable" material which permits vapors to escape from the absorbent core 44 while still preventing liquid exudates from passing through the outer cover 42.

The absorbent core 44 of the absorbent article 30, as representatively illustrated in FIGS. 4–8, may suitably comprise a matrix of hydrophilic fibers, such as a web of cellulosic fluff, mixed with particles of a high-absorbency material commonly known as superabsorbent material. In a particular embodiment, the absorbent core 44 comprises a mixture of superabsorbent hydrogel-forming particles and wood pulp fluff. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the absorbent core 44 may comprise a laminate of fibrous webs and superabsorbent material or other suitable means of maintaining a superabsorbent material in a localized area.

The absorbent core 44 may have any of a number of shapes. For example, the absorbent core may be rectangular, I-shaped or T-shaped. It is generally preferred that the absorbent core be narrower in the crotch portion 36 of the absorbent article 30 than in the front or rear portion, 32 or 34, respectively.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Other suitable absorbent gelling materials are disclosed by Assarson et al. in U.S. Pat. No. 3,902,236 issued Aug. 26, 1975. Processes for preparing synthetic, absorbent gelling polymers are disclosed in U.S. Pat. No. 4,076,663 issued Feb. 28, 1978, to Masuda et al. and U.S. Pat. No. 4,286,082 issued Aug. 25, 1981, to Tsubakimoto et al.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like.

As a general rule, the high-absorbency material is present in the absorbent core in an amount of from about 5 to about 100 weight percent based on total weight of the absorbent core.

The outer cover 42 and bodyside liner 40 are generally adhered to one another so as to form a pocket in which the absorbent core 44 is located. Thus, the leg cuffs 46 are suitably formed by portions of the outer cover 42, and/or bodyside liner 40, which extend beyond the longitudinal sides of the absorbent core 44. Naturally, the leg cuffs 46 can also be formed from separate materials which are attached to the outer cover 42 and/or bodyside liner 40.

The leg cuffs 46, as representatively illustrated in FIGS. 4–8, include leg elastics 48. Materials suitable for use in forming leg elastics 48 are known to those skilled in the art. Exemplary of such materials are strands or ribbons of a polymeric, elastomeric material which are adhered to the absorbent article 30 at the leg cuffs 46 while in a stretched position, or which are attached to the absorbent article while the article is pleated, such that elastic constrictive forces are imparted to the leg cuffs 46.

Similarly, waist elastics 50 and 52 and tape fasteners 54, as representatively illustrated in FIGS. 4–8, are known to those skilled in the art.

A wide variety of infant diaper configurations, as well as training pant, incontinent garment and like configurations, are suitable for use in the present invention. Diapers suitable for use in the present invention are described in greater detail in commonly assigned U.S. patent application Ser. No. 07/757,760 entitled "Thin Absorbent Article Having Rapid Uptake of Liquid" filed Sep. 11, 1991, in the name of Hansen et al.

In a final aspect, the present invention concerns the method of making the absorbent article 30 as representatively illustrated in FIGS. 4–8. The absorbent article 30 includes the containment flaps 10 of the present invention as representatively illustrated in FIGS. 1–3.

A liquid-permeable bodyside liner 40 which has a front portion, a rear portion, and a crotch portion is provided. The crotch portion has opposite longitudinal side portions and connects the front and rear portions. An outer cover 42 is placed in a parallel, facing relationship with the bodyside liner 40. An absorbent core 44 is placed between the bodyside liner 40 and the outer cover 42 and the bodyside liner and outer cover are joined together. A pair of longitudinally extending leg cuffs 46 are formed from the bodyside liner 40 in the crotch portion at the opposite longitudinal side portions. The leg cuffs 46 are elasticized by joining leg elastics 48 to the leg cuffs 46. A pair of barrier layers 20 are provided and stitched with at least one elastomeric thread 22 to form a pair of longitudinally extending containment flaps 10. The containment flaps 10 are joined to the bodyside liner 40 in the crotch portion and the front and rear portions. In a specific embodiment of this method, the barrier layer 20 of the containment flap 10 is stitched with an elastomeric thread 22 that is elongated to a length of from about 200 percent to about 250 percent of its original length.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article having a front portion, a rear portion, and a crotch portion connecting said front and rear portions, said crotch portion having opposite longitudinal side portions, said article comprising:

a) a liquid-permeable bodyside liner;
   b) an outer cover;
   c) an absorbent core located between said bodyside liner and said outer cover;
   d) a pair of elasticized longitudinally extending leg cuffs located in said crotch portion at said opposite longitudinal side portions of said crotch portion; and
   e) a pair of containment flaps which extend longitudinally from said front portion to said rear portion and have a proximal edge joined to said bodyside liner in said crotch portion and said front and rear portions, a distal edge opposite said proximal edge wherein at least a portion of said distal edge is positioned in a spaced relation away from said bodyside liner of said absorbent article towards a generally upright and approximately perpendicular configuration, and a length, each of said containment flaps comprising:
      1) at least one elastomeric thread; and
      2) a barrier layer which is stitched with said at least one elastomeric thread adjacent said distal edge of said containment flap wherein said distal edge of said containment flap is rendered elastically contractible by said at least one elastomeric thread to position said distal edge in said spaced relation.

2. The absorbent article according to claim 1 wherein said barrier layer of said containment flaps comprises a nonwoven material.

3. The absorbent article according to claim 1 wherein said barrier layer of said containment flaps comprises a liquid-impervious film.

4. The absorbent article according to claim 1 wherein said barrier layer of said containment flaps is stitched with said at least one elastomeric thread along said entire length of said containment flaps.

5. The absorbent article according to claim 1 wherein said barrier layer of said containment flaps is stitched with said at least one elastomeric thread along at least about 60 percent of said length of said containment flap.

6. The absorbent article according to claim 1 wherein said at least one elastomeric thread is elongated as said barrier layer is stitched with said at least one elastomeric thread.

7. A method of making an absorbent article comprising the following steps:
   a) providing a liquid-permeable bodyside liner having a front portion, a rear portion, and a crotch portion connecting said front and rear portions, said crotch portion having opposite longitudinal side portions;
   b) placing an outer cover in a facing relationship with said bodyside liner;
   c) placing an absorbent core between said bodyside liner and said outer cover;
   d) joining said bodyside liner to said outer cover;
   e) forming a pair of elasticized longitudinally extending leg cuffs from said bodyside liner in said crotch portion at said opposite longitudinal side portions of said crotch portion;
   f) providing a pair of barrier layers;
   g) stitching each of said barrier layers with at least one elastomeric thread to form a pair of containment flaps; and
   h) joining said containment flaps to said bodyside liner in said crotch portion and said front and rear portions.

8. The method according to claim 7 wherein said at least one elastomeric thread is elongated from about 200 percent to about 250 percent as said barrier layer is stitched with said at least one elastomeric thread.

9. The method according to claim 7 wherein said stitching occurs at a spacing of from about 25 stitches per inch (about 1 stitch per mm) to about 4 stitches per inch (about 1 stitch per 6 mm).

10. The method according to claim 7 wherein said stitching occurs with from 1 to 10 elastomeric threads.

* * * * *